US008512730B2

(12) United States Patent
Seyedin et al.

(10) Patent No.: US 8,512,730 B2
(45) Date of Patent: *Aug. 20, 2013

(54) METHODS OF TISSUE REPAIR AND COMPOSITIONS THEREFOR

(75) Inventors: Mitchell S. Seyedin, Monte Sereno, CA (US); Gary Gage, Chesterfield, MO (US)

(73) Assignee: Isto Technologies, Inc., St. Louis, MO (US)

( * ) Notice: Subject to any disclaimer, the term of this patent is extended or adjusted under 35 U.S.C. 154(b) by 757 days.

This patent is subject to a terminal disclaimer.

(21) Appl. No.: 11/448,701

(22) Filed: Jun. 7, 2006

(65) Prior Publication Data

US 2006/0228391 A1 Oct. 12, 2006

Related U.S. Application Data

(63) Continuation-in-part of application No. 11/179,425, filed on Jul. 11, 2005, now Pat. No. 8,192,759.

(60) Provisional application No. 60/587,088, filed on Jul. 12, 2004.

(51) Int. Cl.
*A61F 13/00* (2006.01)
*A61F 2/00* (2006.01)

(52) U.S. Cl.
USPC .................. 424/423; 424/422; 424/426

(58) Field of Classification Search
None
See application file for complete search history.

(56) References Cited

U.S. PATENT DOCUMENTS

| 4,438,102 | A | * | 3/1984 | Ganci .......................... 424/616 |
| 4,957,744 | A | | 9/1990 | Della Valle et al. |
| 5,290,552 | A | | 3/1994 | Sierra et al. |
| 5,597,897 | A | * | 1/1997 | Ron et al. ..................... 530/350 |
| 5,700,289 | A | * | 12/1997 | Breitbart et al. ............. 424/423 |
| 5,736,372 | A | * | 4/1998 | Vacanti et al. ................ 435/180 |

(Continued)

FOREIGN PATENT DOCUMENTS

| WO | 9300050 | 1/1993 |
| WO | 9401468 | 1/1994 |

(Continued)

OTHER PUBLICATIONS

Benesova, K et al,Stability evaluation of n-alkyl hyaluronic acid derivates by DSC and TG measurement, 2006, Journal of Thermal Analysis and Calorimetry, vol. 83, pp. 341-348.

(Continued)

*Primary Examiner* — Carlos Azpuru
*Assistant Examiner* — Casey Hagopian
(74) *Attorney, Agent, or Firm* — Polsinelli PC

(57) ABSTRACT

The present application discloses matrix compositions to support the repair of tissue defects such as an injury to tendon tissue, ligament tissue, vascular tissue, dermal tissue, or muscle tissue. A matrix described herein comprises a polyester polymer entangled with a polysaccharide polymer. Also disclosed are methods of preparing a matrix, and methods of using a matrix in the repair of tissue. In certain configurations, a matrix can comprise a polyester cross-linked with a polysaccharide, which can be an oxidized polysaccharide. In some configurations, a matrix can further comprise one or more additional components, such as a growth factor or an anti-infective agent. In some configurations, a matrix can be a viscous fluid or a paste, while in other configurations a matrix can be comprised by a solid such as a plug, a granule or a membrane.

17 Claims, 6 Drawing Sheets

(56) References Cited

U.S. PATENT DOCUMENTS

| | | | |
|---|---|---|---|
| 5,769,899 | A | 6/1998 | Schwartz |
| 5,842,477 | A | 12/1998 | Naughton |
| 5,855,608 | A | 1/1999 | Brekke et al. |
| 5,916,585 | A | 6/1999 | Cook |
| 5,972,385 | A | 10/1999 | Liu et al. |
| 6,051,701 | A | 4/2000 | Cialdi et al. |
| 6,281,256 | B1 | 8/2001 | Harris et al. |
| 6,303,585 | B1 | 10/2001 | Spiro et al. |
| 6,328,765 | B1 | 12/2001 | Hardwick et al. |
| 6,339,074 | B1 | 1/2002 | Cialdi et al. |
| 6,344,488 | B1 * | 2/2002 | Chenite et al. ............... 514/777 |
| 6,395,253 | B2 | 5/2002 | Levy et al. |
| 6,454,811 | B1 | 9/2002 | Sherwood et al. |
| 6,579,978 | B1 | 6/2003 | Renier et al. |
| 6,596,274 | B1 | 7/2003 | Abatangelo et al. |
| 6,626,950 | B2 | 9/2003 | Brown et al. |
| 6,673,285 | B2 | 1/2004 | Ma |
| 6,689,747 | B2 | 2/2004 | Filvaroff et al. |
| 6,696,073 | B2 | 2/2004 | Boyce et al. |
| 6,949,252 | B2 | 9/2005 | Mizuno et al. |
| 7,087,745 | B1 | 8/2006 | Pallado et al. |
| 7,446,131 | B1 | 11/2008 | Liu et al. |
| 2002/0004225 | A1 | 1/2002 | Hart et al. |
| 2002/0064559 | A1 | 5/2002 | Lee et al. |
| 2004/0001879 | A1 | 1/2004 | Guo et al. |
| 2004/0033212 | A1 | 2/2004 | Thomson et al. |
| 2004/0078090 | A1 | 4/2004 | Binette |
| 2004/0126405 | A1 | 7/2004 | Sahatjian et al. |
| 2004/0138664 | A1 * | 7/2004 | Bowman ........................ 606/72 |
| 2005/0142163 | A1 | 6/2005 | Hunter et al. |
| 2006/0002979 | A1 * | 1/2006 | Ashammakhi et al. ....... 424/426 |
| 2006/0008530 | A1 * | 1/2006 | Seyedin et al. ............... 424/486 |
| 2007/0128155 | A1 | 6/2007 | Seyedin et al. |

FOREIGN PATENT DOCUMENTS

| | | |
|---|---|---|
| WO | 9531157 | 11/1995 |
| WO | 9628539 | 9/1996 |
| WO | 9628539 A1 | 9/1996 |
| WO | 0101895 | 1/2001 |
| WO | 0135968 | 5/2001 |
| WO | 02072662 A1 | 9/2002 |
| WO | 02076335 | 10/2002 |
| WO | 03039615 | 5/2003 |
| WO | 2006058221 | 6/2006 |

OTHER PUBLICATIONS

Wang, Z.G. et al, Morphological development in absorbable poly(glycolide), poly(glycolide-co-lactide), and poly (glycolide-co-cprolactone) copolymers during isothermal crystallization, 2000, Polymer, vol. 41, pp. 621-628.

Office Action issued Aug. 27, 2010 regarding U.S. Appl. No. 11/179,425, 16 pages.

Office Action issued Dec. 23, 2009 regarding U.S. Appl. No. 11/179,425, 17 pages.

Office Action issued Feb. 23, 2009 regarding U.S. Appl. No. 11/179,425, 25 pages.

Office Action issued Apr. 15, 2010 regarding U.S. Appl. No. 11/179,425, 16 pages.

Office Action issued Nov. 29, 2010 regarding U.S. Appl. No. 11/179,425, 9 pages.

International Search Report dated Sep. 16, 2008 regarding PCT/US07/70631, 6 pages.

Search Report regarding European Application No. EP05812025.4 dated Feb. 7, 2012, 6 pages.

Notice of Allowance and Fees Due regarding U.S. Appl. No. 11/179,425 with the mailing date of May 6, 2011, 13 pages.

De Gennes, P.G., Reptation of a Polymer Chain in the Presence of Fixed Obstacles, Journal of Chemical Physics, 1971, pp. 572-579, vol. 55, No. 2.

Edwards, S.F., The statistical mechanics of polymerized material, Proc. Phys. Cos, 1967, pp. 9-16, vol. 92.

Office Action regarding U.S. Appl. No. 11/635,265 issued Dec. 8, 2009, 8 pages.

Office Action regarding U.S. Appl. No. 11/635,265 issued May 12, 2010, 17 pages.

International Search Report regarding European National Application No. 05812025.4, issued Dec. 14, 2009, 1 page.

International Search Report regarding PCT/US2006/04576, issued Oct. 22, 2008, 1 page.

Benjamin, M. and Ralphs, J.R., Biology of Fibrocartilage Cells, International Review of Cytology, 2004, pp. 1-45, vol. 233.

Fu, F.H. et al, Autologous Chondrocyte Implantation Versus Debridement for Treatment of Full-Thickness Chondral Defects of the Knee, American Journal of Sports Medicine, An Observational Cohort Study With 3-Year Follow-up, 2005, pp. 1658-1666, vol. 33, No. 11.

Gilbert, J.E., Current Treatment Options for the Restoration of Articular Cartilage, American Journal of Knee Surgery, 1998, pp. 42-46, vol. 11, No. 1.

Gombotz, W.R. and Pettit, D.K., Biodegradable Polymers for Protein and Peptide Drug Delivery, Bioconjugate Chem., 1995, pp. 3320351, vol. 6.

Gross, A. E., Cartilage Resurfacing, Journal of Arthroplasty, 2003, pp. 14-17, vol. 18, No. 3, Suppl. 1.

Helmsworth, T.F. et al, Molecular Surgery of the Basement Membrane by the Argon Laser, Lasers in Surgery and Medicine, 1990, pp. 576-583, vol. 10.

Hunziker, E.B., Articular cartilage repair: basic science and clinical progress. A review of the current status and prospects, Osteoarthritis and Cartilage, 2001, pp. 432-463, vol. 10.

Minas, T. and Nehrer, S., Current Concepts in the Treatment of Articular Cartilage Defects, Orthopedics, 1997, pp. 525-538, vol. 20, No. 6.

Steadman, J.R. et al, Microfracture: Surgical Technique and Rehabilitation to Treat Chondral Defects, Clinical Orthopaedics and Related Research, 2001, pp. S362-S369, vol. 391S.

Vangsness, C.T. et al, Restoring articular cartilage in the knee, Am. J. Orthop., 2004, pp. 29-34, vol. 33, No. 2S.

Examination Report regarding Australian Application No. 2005287402 issued Aug. 26, 2009, 2 pages.

Office Action regarding Japanese Patent Application No. 2007-521541 issued Dec. 22, 2010, 7 pages.

European Search Opinion regarding European Application No. 06839104.4 issued Dec. 23, 2009, 19 pages.

Uematsu, K. et al, Cartilage regeneration using mesenchymal stem cells and a three-dimensional poly-lactic-glycolic acid (PLGA) scaffold, Biomaterials, 2005, pp. 4273-4279, vol. 26, No. 20.

English translation of claims for Japanese Application No. 7-157439 as provided by foreign associate on Jan. 2011, 4 pages.

Hyaluronan—Modified Surfaces for Medical Devices, www.devicelink.com/grabber.php3?URL=http://www.devicelink.com/mddi/archive . . . , MD&D column, 1999, 15 pages.

Amiel et al., "Rib Perichondrial Grafts for the Repair of Full-Thickness Articular-Cartilage Defects," J. Bone Joint Surg. 67A:911-920 (1985).

Blein-Sella et al., "Rabbit Articular Chondrocyte Functional Toxicity Test," Methods Mol. Biol. 43:169-175 (1995).

Dietz et al., "Alterations of Collagen mRNA Expression During Retinoic Acid Induced Chondrocyte Modulation: Absence of Untranslated α1(I) mRNA in Hyaline Chondrocytes," J. Cell Biol. 52:57-68 (1993).

Fukuzaki et al., "In vivo Characteristics of Low Molecular Weight Copolymers Composed of L-lactic Acid and Various DL-hydroxy Acids as Biodegradable Carriers for Drug Delivery Systems," Biomaterials 11:441-446 (1990).

Hollinger, "Preliminary Report on the Osteogenic Potential of a Biodegradable Copolymer of Polyactide (PLA) and Polyglycolide (PGA)," J. Biomed. Mater. Res. 17: 71-82 (1983).

Jalil, "Biodegradable poly(lactic acid) and poly(lactide-co-glycolide) Microcapsules: Problems Associated with Preparative Techniques and Release Properties," J. Microencapsulation 7:297-325 (1990).

Kuettner, "Biochemistry of Articular Cartilage in Health and Disease," Clin. Biochem. 25: 155-163 (1992).

Kuo, "Chemical Modification of Hyaluronic Acid by Carbodimides," Bioconjugate Chem. 2: 232-241 (1991).

Mason, :"Attachment of Hyaluronic Acid to Polypropylene, Polystyrene, and Polytetrafluoroethylene," Biomaterials 21: 31-36 (2000).

Sierra et al., "Fibrin-Collagen Adhesive Drug Delivery System for Tumor Therapy," Trans. Soc. Biomater. 16: 257 (1993).

Zhao, "Synthesis and Characterization of a Novel Double Crosslined Hyaluronan Hydrogel," J. Mater. Sci. Mater. Med. 13: 11-16 (2002.

* cited by examiner

METHODS OF TISSUE REPAIR AND COMPOSITIONS THEREFOR

CROSS-REFERENCE TO RELATED APPLICATIONS

This application is a continuation-in-part of, and claims benefit of priority to, U.S. patent application Ser. No. 11/179,425 filed Jul. 11, 2005, which claims benefit of priority to provisional application No. 60/587,088 filed Jul. 12, 2004. These applications are hereby incorporated by reference in their entireties.

BACKGROUND

There is a clinical demand for biocompatible matrices that offer tissue growth-conductive and or growth-inductive properties resembling those of autologous tissue and that can be produced in unlimited supply, for tissues such as bone, cartilage, connective tissue or soft tissue. Although some bone substitutes are available, many consist of materials that have poor physical handling and resorption characteristics that complicate their use and radiographic evaluation.

U.S. Pat. No. 6,673,285 to Ma, issued Jan. 6, 2004 discloses 3-D biodegradable porous, polymer (natural or synthetic) scaffolds with well-controlled, interconnected pores, and method for forming the porous materials. This patent further discloses fabricating hydrophilic and/or hydrophobic porogen materials into 3-D negative replicas of the desired macroporous architectures. In the methods, biodegradable polymers (PLLA and PLGA) are dissolved in a solvent and cast onto the negative replica. After dissolving/leaching out the porogen materials, a porous polymer scaffold is formed.

U.S. Pat. No. 5,769,899 to Schwartz, issued Jun. 23, 1998, discloses a bio-absorbable cartilage repair system for regenerating damaged or destroyed articular cartilage on the surface of a bone by establishing a chondrogenic growth-supporting matrix between an area of removed damaged or destroyed articular cartilage and the adjacent healthy cancellous bone. The repair system comprises a delivery unit consisting substantially of completely bio-absorbable material which is dimensionally stable against substantial expansion by absorption of synovial joint fluid, and configured and dimensioned to be mounted in both an area of damaged or destroyed articular cartilage that has been removed and an adjacent healthy area of articular cartilage and subchondral cancellous bone; and a porous insert supported by the delivery unit, consisting substantially of completely bio-absorbable material, and defining at least 95% voids by volume for establishing communication between the removed area and the adjacent healthy area for a chondrogenic growth-supporting matrix. The delivery unit can comprise polyester, and the porous insert can comprise hyaluronic acid.

U.S. Pat. No. 5,842,477 to Naughton, issued Dec. 1, 1998, discloses methods of making and/or repairing cartilage in vivo which include implanting into a patient a biocompatible, non-living three-dimensional scaffold which can be made from a material such as polyglycolic acid, polylactic acid or hyaluronic acid.

U.S. Pat. No. 5,916,585 to Cook, issued Jun. 29, 1999, discloses a biodegradable material for immobilization of bioactive species thereon. The material comprises a porous hydrophobic biodegradable support member which can be polyglycolide or a copolymer of glycolide, glycolide/L-lactide, and at least one layer of a hydrophilic polymer.

U.S. Pat. No. 6,328,765 to Hardwick, issued Dec. 11, 2001, discloses a tissue penetrable device constructed of degradable materials such as non-highly cross-linked hyaluronic acid, a hydrolyzable polyester such as polylactic acid and polyglycolic acid, or a blend thereof.

U.S. Pat. No. 6,696,073 to Boyce, issued Jan. 28, 2003, discloses a load-bearing osteoimplant comprising a shaped, coherent mass of bone particles and a binder, which can comprise a polysaccharide, polylactic acid, polyglycolic acid, polylactic-co-glycolic acid, polylactide, polyglycolide, or poly(lactide-co-glycolide).

US Patent application publication 20040126405 of Sahajian, published Jul. 1, 2004, discloses a three dimensional cell scaffold including a biocompatible polymer formed from a plurality of fibers configured so as to form a non-woven three dimensional open celled matrix having a predetermined shape, a predetermined pore volume fraction, a predetermined pore shape, and a predetermined pore size, with the matrix having a plurality of connections between the fibers. The biodegradable polymer can be poly L-lactic acid, polyglycolic acid (PGA), hyaluronic acid, or a copolymer or blend thereof.

US Patent application publication 20040078090 of Binette, published Apr. 22, 2004, discloses a biocompatible tissue repair implant or scaffold device for use in repairing a variety of tissue injuries, particularly injuries to cartilage, ligaments, tendons, and nerves. The implant includes a biocompatible scaffold and particles of living tissue. The biocompatible scaffold can include homopolymers or copolymers of lactides or glycolides, and hyaluronic acid as an adhesion agent.

US patent application publication 20060067971 of Story and US patent application 20060067973 of Schacter, both published Mar. 30, 2006, disclose bone void filler compositions comprising a biodegradable material, an osteoconductive component, and a therapeutically effective amount of a therapeutic agent.

None of these references recites a matrix comprising a polyester entangled with a polysaccharide. Accordingly, there remains a need for biodegradable, biocompatible matrices which maintain structural integrity and which can be used in the repair tissues such as bone, cartilage, connective tissue and/or soft tissue.

SUMMARY

In view of the need for biodegradable, biocompatible matrices for use in repairing tissues, the present inventors have developed matrix compositions that support the repair of tissue. Furthermore, the inventors have developed methods for preparing such matrices, and methods of treatment that utilize the matrices. In addition, the inventors disclose the use of matrices comprising a polyester entangled with a polysaccharide for the manufacture of a medicament for promoting tissue growth.

Accordingly, the present teachings disclose matrices for supporting the repair of a tissue. A matrix of embodiments of these teachings comprises a polyester entangled with a polysaccharide. In some aspects, a matrix can be comprised by an implant, which can have, in various embodiments, the shape of a fastener, a prosthesis, a substantially anatomical shape, a substantially geometric shape, or a combination thereof. In some configurations, a matrix of these embodiments can further comprise at least one growth factor, which can be an epithelial growth factor (EGF), a vascular endothelial growth factor (VEGF), a transforming growth factor-β (TGF-β), a bone morphogenetic protein (BMP), a growth differentiation factor, an anti-dorsalizing morphogenetic protein-1 (ADMP-1), a basic fibroblast growth factor (bFGF), an acidic fibroblast growth factor (aFGF) a hedgehog protein, an insulin-like growth factor, a platelet-derived growth factor (PDGF), an interleukin (IL), a colony-stimulating factor (CSF), and/or an activin. In addition, a matrix of these embodiments can further comprise a collagen.

In various aspects, a matrix disclosed here can have a viscosity ranging from about 200,000 centipoise to about $3 \times 10^{10}$ centipoise at 20° C. In certain other aspects, viscosity of a matrix at 20° C. can range from about $10^6$ centipoise to about $10^9$ centipoise at 20° C., while in yet other aspects, the viscosity of a matrix can range from about $10^7$ centipoise to about $10^8$ centipoise at 20° C.

Various embodiments of the present teachings include matrices which comprise not only a polyester entangled with a polysaccharide, but also further comprise at least one therapeutic agent. In these embodiments, a therapeutic agent can be, without limitation, an anti-infective agent, a pain medication, an analgesic, or anti-inflammatory agent, and an immunosuppressive agent.

In various aspects, an anti-infective agent which can be comprised by a matrix of the present teachings can be an antibiotic such as gentamicin, dibekacin, kanendomycin, lividomycin, tobramycin, amikacin, fradiomycin, sisomicin, tetracycline, hydrochloride, oxytetracycline, hydrochloride, rolitetracycline, doxycycline hydrochloride, ampicillin, piperacillin, ticarcillin, cephalothin, cephaloridine, cefotiam, cefsulodin, cefinenoxime, cefinetazole, cefazolin, cefotaxime, cefoperazone, ceftizoxime, moxolactam, latamoxef, thienamycin, sulfazecin, azthreonam or a combination thereof.

In various configurations of the disclosed embodiments, a polysaccharide can be hyaluronic acid, chondroitin sulfate, dermatan sulfate, keratan sulfate, heparan, heparan sulfate, dextran, dextran sulfate, alginate, or a combination thereof. In addition, a polyester of a matrix can be polylactic acid, polyglycolic acid, or a co-polymer comprising polylactic acid and polyglycolic acid. Furthermore, a polysaccharide comprised by a matrix can be both entangled with a polyester, and cross-linked. In some configurations of a matrix comprising a cross-linked polysaccharide, the polysaccharide can be an oxidized polysaccharide. In some alternative configurations, the polysaccharide can be cross-linked via a cross-linking agent. In addition, in various configurations, a cross-linked matrix can include, not only a cross-linked polysaccharide and a polyester, but also a growth factor and/or a collagen. Matrices can be of various viscosities, so that in some configurations, a matrix can be suitable for injection or suitable for implantation.

Methods of preparing a matrix of the present teachings comprise entangling, in a mixture, a polyester and a polysaccharide. A method of preparing a matrix can further comprise cross-linking a polysaccharide. Cross-linking can include oxidizing a polysaccharide, and/or contacting a polysaccharide with a cross-linking agent. The oxidizing and/or the contacting of a polysaccharide with a cross-linking agent can be effected either before or after entangling a polysaccharide with a polyester. In addition, a method of preparing a matrix can further include adding to a mixture at least one growth factor and/or a collagen.

The present inventors have also developed methods for promoting tissue growth in a mammal, such as a human patient in need of treatment. A human patient in need of treatment can include a person suffering from a traumatic injury, a disease, a birth defect and/or a genetic defect, and/or a person desirous of a cosmetic change. In various embodiments, the methods comprise administering to the mammal, at a site in need of tissue growth, a matrix described herein. In various aspects, administering a matrix can comprise surgical implantation of a matrix and/or injection of a matrix at a site in need of tissue growth and/or repair. Promoting tissue growth and/or repair can include conducting tissue growth, and/or inducing tissue growth. In various aspects, a site in need of tissue growth can comprise tendon tissue, ligament tissue, vascular tissue, dermal tissue, periodontal tissue such as a periodontal ligament, intervertebral disc tissue, hyaline cartilage, fibrous cartilage, elastic cartilage, a nerve tunnel or a combination thereof.

In various aspects, the methods include administration of a matrix described herein by surgical implantation and/or injection into or adjacent to the muscle tissue of a patient. These methods can thus be used, in some aspects, to stimulate muscle growth and/or repair in an individual patient in need, such as a person experiencing loss of muscle mass resulting from a disease having symptoms of dystrophic or atrophic muscle, such as, without limitation, AIDS, muscular dystrophy, diabetes or cancer.

In various aspects, methods of administering to a subject a matrix described herein can include injecting the matrix and/or implanting the matrix into the subject. In various configurations, a site in need of tissue growth can comprise, without limitation, dermis, a rotator cuff tendon, an Achilles tendon, a ligament such as an anterior cruciate ligament (ACL), a posterior cruciate ligament, (PCL), a medial collateral ligament, a lateral collateral ligament or a periodontal ligment, a sphincter such as an anal sphincter, a urethral sphincter, an esophageal sphincter or an antral sphincter, herniated tissue such as an abdominal hernia, a Cooper's hernia, a diaphragmatic hernia, an epigastric hernia, a femoral hernia, an incisional hernia, an inguinal hernia, an intervertebral disc hernia, a Littre's hernia, an obturator hernia, a pantaloon hernia, a perineal hernia, a properitoneal hernia, a Richter's hernia, a sciatic hernia, a sliding hernia, a Spigelian hernia or an umbilical hernia, an intervertebral disc nucleus, an intervertebral disc annulus, periosteal tissue, neural tissue such as central nervous system tissue (including spinal cord tissue) and demyelinated neural tissue, a nerve tunnel such as a nerve tunnel traversing bone tissue, a mitral valve, a tricuspid valve, an aortic heart valve, a pulmonary heart valve, vascular tissue comprising a stent, stenotic cardiovascular tissue, costal cartilage, meniscus cartilage, epiglottic cartilage, laryngeal cartilage such as arytenoid cartilage, cricoid cartilage, cuneiform cartilage and corniculate cartilage, external ear cartilage, or auditory tube cartilage.

In various configurations, the methods and matrices disclosed herein can be used in facial contour augmentation, such as the repair of facial features or reduction of skin folds or wrinkles. Similarly, in some aspects the methods and matrices can be used for repairing scar tissue. Accordingly, in various aspects, methods comprise implantation and/or injection of a matrix into or adjacent to the dermis of a patient, such as facial dermis. In some configurations, these methods can thus be used, without limitation, for facial augmentation, such as amelioration of facial skin folds, for examples skin folds resulting from aging and/or exposure to excess sunlight.

In various aspects of the present teachings, the methods further include securing a matrix with a fastener at an implantation site. Accordingly, some aspects include an implant comprising a matrix of the present teachings, wherein the implant can be a fastener or a prosthesis. In related aspects, an implant can comprise a fastener comprising a matrix of the present teachings. In some aspects, a fastener can be, without limitation, a staple, a dart, a pin, a screw, a suture, a glue or a tack. In other aspects, a prosthesis can be a prosthetic plate.

In various embodiments of the present teachings, a matrix comprising a polyester entangled with a polysaccharide can be comprised by an implant which comprises a substantially anatomical shape or a substantially geometric shape. In these embodiments, a substantially geometrical shape can be, without limitation, a substantially cylindrical shape, a substantially pyramidal shape or a substantially frustoconical shape, and a substantially anatomical shape can be, without limitation, that of a condyle, a hemi-condyle, an acetabular cup, a tibial plateau or a femoral head. In some embodiments, a substantially anatomical shape can be a substantially anatomical shape, such as that of bone such as a maxilla, a mandible, a temporal bone, a sphenoid bone, a frontal bone or a zygoma. In some embodiments, a substantially anatomical shape can be a substantially dental shape, such as a molar tooth, a canine tooth or an incisor tooth.

In various aspects of the present teachings, a matrix comprising a polyester entangled with a polysaccharide can be comprised by a solid such as a plug, a granule, or a membrane. Furthermore, in some embodiments, a matrix can be in an injectable form, e.g., as a slurry, a paste or a viscous fluid. The a matrix of these embodiments can have a viscosity ranging from about from about 200,000 centipoise to about $3 \times 10^{10}$ centipoise at 20° C., from about $10^6$ centipoise to about $10^9$ centipoise at 20° C., or from about $1.5 \times 10^6$ centipoise to about $10^8$ centipoise at 20° C. In addition, in some configurations, a matrix can be comprised by a paste. In some configurations, a matrix can be applied as a paste in a therapeutically effective amount to a defect site in a subject in need of treatment.

In yet other aspects, a paste comprising a matrix can be used in performing an interbody fusion. In these aspects, a therapeutic method for performing an interbody fusion can comprise inserting an interbody cage in the spine of a patient in need of treatment, and filling the cage with a therapeutically effective amount of a paste comprising a matrix of the present teachings. In certain aspects, an interbody fusion can be a lumbar interbody fusion such as an anterior lumbar interbody fusion or a posterior lumbar interbody fusion, or a cervical interbody fusion.

In various embodiments, the present teaching include methods of preparing a paste comprising a matrix of the present teachings. In various aspects of these embodiments, a method comprises forming a mixture comprising a matrix comprising a polyester entangled with a polysaccharide as described herein, and a liquid such as an aqueous liquid. In various aspects, the matrix can be particulate. Furthermore, in various aspects, an aqueous liquid can be water, a saline such as physiological saline, blood such as that of a human subject, serum, plasma, a hyaluronic acid solution (such as a 1%-2% w/w solution of hyaluronic acid), and/or a protein solution, such as fibrin solution (such as a biological glue comprising fibrin). Pastes of different viscosities can be prepared by varying the weight ratios of the components in a mixture.

These and other features, aspects, and advantages of the present invention will become better understood with regard to the following description and appended claims.

DETAILED DESCRIPTION

Figure 1:
FIG. 1 illustrates a introduction of a circular defect in a medial femoral condyle of a sheep, and introduction of a matrix into the defect.
Figure 1:

The present inventors have devised matrices for supporting repair of a tissue. The inventors have also devised methods for preparing the matrices, methods of using the matrices for promoting growth and repair of tissue, and use of the matrices for the manufacture of medicaments for supporting tissue repair.

An entangled polyester-polysaccharide matrix of the present invention may be used alone to conduct the growth of tissue, in combination with at least one growth factor to induce the growth of tissue, in combination with cells to induce the growth of tissue, in combination with cells to induce the growth of tissue, and/or in combination with a collagen or fibrin, and/or in combination with one or more therapeutic agents. "Entanglement" and related terms, as used herein, refers to a state of polymers in melts or concentrated solutions above the overlap concentration, in which polymers interpenetrate one another and motion of the molecules is restricted to movement along a 'virtual tube' which surrounds each molecule (Adrian R. Rennie, Glossary of Colloid and Polymer Science).

In various embodiments of the present teachings, membranes comprising a polyester entangled with a polysaccharide, and methods of making such membranes, are described in U.S. patent application Ser. No. 11/179,425, "Tissue Matrix System," filed Jul. 11, 2005, Publication No. 20060008530 A1, which is incorporated herein by reference in its entirety.

Accordingly, a matrix of the present teachings comprises a polyester entangled with a polysaccharide. A polyester comprised by a matrix can be polylactic acid (PLA), polyglycolic acid (PGA), or a copolymer comprising PLA and PGA (also referred to as poly(lactide-co-glycolide, PLA-PGA, or PLGA). A polyester such as a PLGA co-polymer can be a biodegradable co-polymer. In some configurations, a PLGA co-polymer comprised by a matrix can comprise PLA and PGA in a weight ratio of about 5:1 to about 2:1, and, in certain aspects, the PLA:PGA ratio can be about 3:1 by weight. A PLA-PGA co-polymer can be, for example, a polyester such as a PLGA co-polymer described in Hollinger, J. Biomed. Mater. Res. 17: 71-82, 1983.

In some configurations, a matrix of the present teachings can be a viscous liquid. The viscosity of a liquid form of a matrix can be such that the matrix can be introduced to a target site in a body by a medical practitioner by well known techniques such as injection through a standard medical injection device such as, for example, a syringe fitted with a hypodermic needle. In these configurations, a matrix can have a viscosity ranging from about 200,000 centipoise to about $3 \times 10^{10}$ centipoise at 20° C., from about $10^6$ centipoise to about $10^9$ centipoise at 20° C., or from about $10^7$ centipoise to about $10^8$ centipoise at 20° C.

In various configurations, a polysaccharide comprised by a matrix can be hyaluronic acid, chondroitin sulfate, dermatan sulfate, keratan sulfate, heparin, heparan sulfate, dextran, dextran sulfate, or alginate. In some aspects, a matrix can comprise a combination of two or more of these polysaccharides. In certain aspects, the polysaccharide can be hyaluronic acid.

In some configurations of a matrix, a polysaccharide can be a cross-linked polysaccharide. The cross-linkage can include any type of cross-linkage known to skilled artisans, for example as disclosed in references such as Laurent, T. C., Acta Chem. Scand. 18: 274-275, 1964; Kuo, J.-W Bioconjugate Chem. 2: 232-241, 1991; Mason, M., Biomaterials 21: 31-36, 2000; or Zhao, X. B., J. Mater. Sci. Mater. Med. 13: 11-16, 2002, and can include an aldehyde cross-linking agent such as formaldehyde or glutaraldehyde, a homobifunctional cross-linking agent or a heterobifunctional cross-linking agent such as a polysaccharide-reactive cross-linking agent. In various aspects, a cross-linkage can comprise an oxidized polysaccharide, such as a periodate-oxidized polysaccharide. In some configurations, a cross-linkage can comprise a covalent attachment between a polysaccharide and a polyester, or between a polysaccharide and any other matrix component described herein.

In a matrix of the present teachings, the weight ratio of polyester to polysaccharide can be between 99:1 to 1:99. In some aspects, the weight ratio of the polyester to the polysaccharide can be from about 9:1 to about 1:9.

In some configurations, a matrix of the present teachings can comprise, in addition to a polyester and a polysaccharide, at least one growth factor. A growth factor which can be comprised by a matrix can be, in non-limiting example, an epithelial growth factor (EGF), a vascular endothelial growth factor (VEGF), a member of the TGF-β superfamily, such as TGF-β1, TGF-β2, TGF-β3, or a bone morphogenetic protein (BMP); a growth differentiation factor; anti-dorsalizing morphogenetic protein-1 (ADMP-1); a fibroblast growth factor (FGF) such as acidic FGF or basic FGF; a member of the hedgehog family of proteins, such as indian hedgehog, sonic hedgehog, or desert hedgehog; an interleukin (IL); a colony-stimulating factor (CSF); an activin; a member of the insulin-like growth factor (IGF) family, such as IGF-I or IGF-II; a platelet-derived growth factor (PDGF) such as PDGF-AP, PDGF-BB and PDGF-AA; a member of the interleukin (IL) family, such as IL-1, IL-2, IL-3, IL-4, IL-5 or IL-6; or a member of the colony-stimulating factor (CSF) family, such as CSF-1, G-CSF, and GM-CSF. A growth factor comprised by a matrix can be a growth factor obtained from a tissue source, or can be a recombinant growth factor produced in vitro, in a cell culture, or in a microorganism using standard molecular biology techniques. In some aspects, a growth factor can be a bone morphogenetic protein, such as, in non-limiting example, BMP-1, BMP-2, BMP-3, BMP-4, BMP-5, or BMP-6. In addition, a matrix can also include at least one collagen, such as, in non-limiting example, type I collagen, type IX collagen, type X collagen, or type XI collagen. Furthermore, in some embodiments, a matrix can also include one or more therapeutic agents, such as a pain medication, an anti-infective agent, an analgesic, an anti-inflammatory agent, or an immunosuppressive agent. Non-limiting examples of a therapeutic agent which can be comprised by a matrix include morphine, a nonsteroidal anti-inflammatory (NSAID) drug, oxycodone, morphine, fentanyl, hydrocodone, naproxyphene, codeine, acetaminophen, benzocaine, lidocaine, procaine, bupivacaine, ropivacaine, mepivacaine, chloroprocaine, tetracaine, cocaine, etidocaine, prilocalne, procaine, clonidine, xylazine, medetomidine, dexmedetomidine, and a VR1 antagonist.

The present inventors have also developed methods for preparing the matrices described herein. The methods described herein utilize laboratory techniques well known to skilled artisans, and guidance can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999, and textbooks such as Hedrickson et al., Organic Chemistry $3^{rd}$ edition, McGraw Hill, New York, 1970.

Accordingly, methods of the present teachings comprise forming a mixture comprising a polyester and a polysaccharide, and entangling the polyester and the polysaccharide in the mixture. Entangling a polysaccharide with a polyester can be effected by any method known to those of skill in the art, such as, in non-limiting example, the method described in Example 1 below.

In making a matrix, a polysaccharide is entangled with a polyester comprising polylactic acid, polyglycolic acid, or a co-polymer comprising polylactic acid and polyglycolic acid. When a polyester is a co-polymer comprising PLA and PGA, the component polymer acids can be in a weight ratio (PLA: PGA) of about 5:1 to about 2:1, such as about 3:1. A co-polymer can be obtained from a commercial supplier, or can be prepared according to well-known techniques, as described in references such as, in non-limiting example, Fukuzaki, Biomaterials 11: 441-446, 1990 and Jalil, J. Microencapsulation 7: 297-325, 1990.

In various aspects, a method for forming a matrix can further comprise oxidizing the polysaccharide. The oxidation can utilize any method for oxidizing a polysaccharide known to skilled artisans, such as, for example periodate oxidation. Oxidizing a polysaccharide can comprise oxidizing sugar rings on the polysaccharide, and can be effected either before or after entangling the polysaccharide with a polyester.

Preparing a matrix can also comprise, in some embodiments, covalently cross-linking a polysaccharide component of a matrix. The cross-linking of a polysaccharide can be effected either before or after forming a mixture with a polyester, or entangling the polyester with the polysaccharide. In some configurations, cross-linking can be effected using an oxidized polysaccharide. In addition, in some aspects, cross-linking can be effected by contacting a polysaccharide with a chemical cross-linker, such as, in non-limiting example, an aldehyde cross-linking agent such as formaldehyde or glutaraldehyde, a homobifunctional cross-linking agent or a heterobifunctional cross-linking agent such as a polysaccharide-reactive cross-linking agent supplied commercially by sources such as Pierce Biotechnology Inc. (Rockford Ill.) or Molecular Probes/Invitrogen Corporation, (Carlsbad, Calif.).

Preparation of a matrix can comprise forming a mixture wherein the polyester and the polysaccharide are combined in a mixture in a weight ratio ranging from about 99:1 to about 1:99; methods of these embodiments can include adding the polyester and the polysaccharide in a weight ratio of from about 9:1 to about 1:9. A skilled artisan, in non-limiting example, can determine by routine experimentation an optimal ratio of polyester to polysaccharide with respect to physical, chemical, or biological properties of a resulting entangled matrix, such as, in non-limiting example, adhesiveness towards cells, resorption characteristics, stability, flexibility, strength, biocompatibility, injectability, viscosity and adsorptiveness for macromolecules such as serum proteins or extracellular matrix components. The macromolecular components of a mixture can be entangled by methods well-known to skilled artisans, which can include, in some aspects, freezing and lyophilizing a mixture comprising a polyester and a polysaccharide, or wet laying and air drying the mixture.

Forming a matrix of the present teachings can further comprise adding to a mixture comprising a polyester and a polysaccharide, at least one growth factor, such as those listed above, and in particular, a bone morphogenetic protein (BMP). The amount and species of a growth factor to add to a mixture can be determined by a skilled artisan by routine experimentation, and can be varied according to the intended use of a matrix. In non-limiting example, a bone morphogenetic protein can be added to a mixture comprising a polyester and a polysaccharide to form a matrix which can be used to stimulate bone growth. Forming a matrix can also comprise adding a collagen to a mixture. The collagen can be any type of collagen, such as those listed above. Forming a matrix can also comprise adding a therapeutic agent to a mixture. The therapeutic agent can be any type of therapeutic agent, such as those listed above.

In various embodiments, the present teachings include methods for promoting tissue growth in a subject. These methods comprise administering in the subject, at a site in need of tissue growth, a matrix comprising a polyester entangled with a polysaccharide, as described herein. A subject in these embodiments can be a mammal, such as, without limitation, a human, in particular a human patient in need of treatment, a companion animal, or a farm animal. A matrix in these embodiments can further comprise at least one growth factor and/or at least one collagen and/or at least one therapeutic agent. In various configurations, a tissue can be, without limitation, bone, cartilage, tendon tissue, ligament tissue, soft tissue such as vascular tissue, dermal tissue or muscle tissue, or a combination thereof. In some other configurations, a site in need of tissue growth can comprise tendon tissue, ligament tissue, vascular tissue, dermal tissue, periodontal tissue, intervertebral disc tissue, hyaline cartilage, fibrous cartilage, elastic cartilage, a nerve tunnel or a combination thereof. Accordingly, a mammalian recipient of a matrix of the present teachings can be a human patient in need of treatment, such as, in non-limiting example, an individual having an injury or degenerative disease of bone, cartilage, tendon tissue, ligament tissue, vascular tissue, dermal tissue, muscle tissue or a combination thereof. In these embodiments, a skilled artisan such as a surgeon or a dermatologist can implant or inject a matrix at a site within the body of the patient. The introduced matrix can accelerate or promote the healing of adjacent tissue. In non-limiting example, a human in need of treatment can be a patient having muscle atrophy or dystrophy resulting from a disease or disorder such as AIDS, diabetes, muscular dystrophy or cancer. In another non-limiting example, a subject in need of treatment can be a human in need of skin augmentation, such as, for example, a subject such as a patient having a dermal disorder such as skin folds due to aging and/or ultraviolet light exposure. An ameliorating treatment can comprise administering a matrix of the present teachings to the dermis of the patient, such as the patient's facial dermis. The administering can include, in non-limiting example, injection of an injectable form of a matrix adjacent to the skin targeted for skin augmentation. In yet another non-limiting example, a human in need of treatment can be a patient recovering from a traumatic injury to an internal organ which requires revascularization. In such an individual, growth of new blood vasculature can be directed and/or promoted by surgical implantation or injection of a matrix.

In various embodiments, the present teachings also encompass the use of a matrix for the manufacture of a medicament for promoting tissue growth. A matrix of these embodiments comprises a polyester entangled with a polysaccharide, as described herein. Manufacture of a medicament can comprise the disclosed methods of forming a matrix.

The following examples are illustrative, and are not intended to limit the scope of the claims. The description of a composition or a method in an example does not imply that a described article or composition has, or has not, been produced, or that a described method has, or has not, been performed, irrespective of verb tense used.

EXAMPLES

Example 1

This example illustrates a method of constructing an entangled matrix comprising a polyester and a polysaccharide.

In this example, poly(lactide-co-glycolide) (PLGA) having molecular weight of about $1.5 \times 10^5$ is dissolved in dichloromethane (125 mg/ml), and Hyaluronate (HA) of molecular weight of about $1.3 \times 10^6$ Dalton is dissolved in water (15 mg/ml). The two polymer solutions, 2 parts PLGA, and 1 part HA, are mixed with 1 part Milli Q water by vortexing at high speed for about 5 minutes. The emulsified mixture is immediately poured into a mold pre-cooled at −70 C in a bath containing dry ice in isopropyl alcohol. After freezing, the mold and its contents are transferred into a second container that is loaded with dry ice and connected to a vacuum line. Organic solvent is removed by this process at the temperature between −70 C to −40 C, leaving HA in wet-ice phase. Water is then removed by raising the temperature to −10 C under vacuum, yielding a matrix comprising a polyester entangled with a hyaluronate polysaccharide.

Example 2

This example illustrates implant site preparation and post-implantation of a matrix in an animal model experimental system.

In this example, as shown in FIG. 1, a circular defect was created in the weight-bearing region of the medial femoral condyle of a skeletally mature sheep using a 5.5 mm diameter OATS-type punch to a depth of 6 mm in an animal model of an osteochondral defect (FIG. 1a). The defect was then flushed with sterile saline prior to insertion of a test matrix. An entangled polyester-polysaccharide matrix comprising PLA-PGA copolymer and hyaluronic acid as described in Example 1 was then press-fit into the defect using a blunt instrument. FIG. 1b shows the implant site post-implantation.

Example 3

Figure 2:
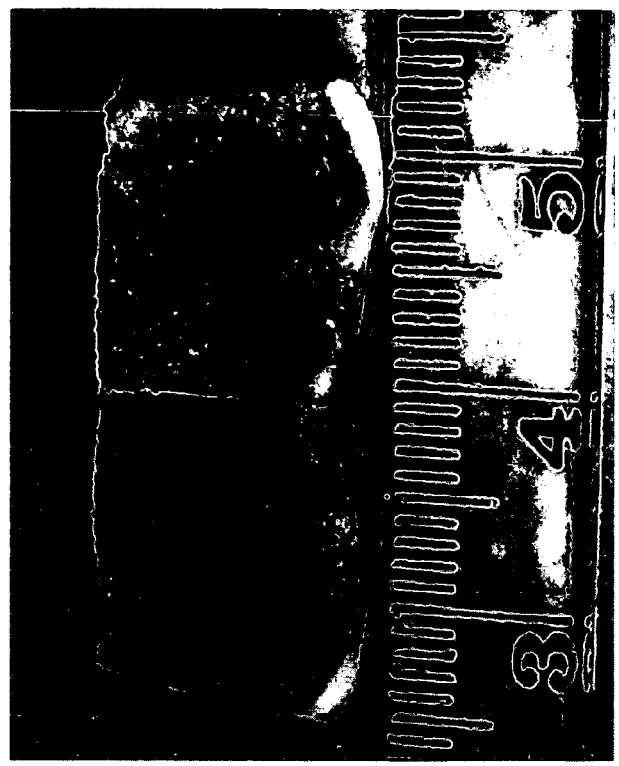
FIG. 2 illustrates gross morphology in a medial femoral condyle of a sheep three months after introduction of a circular defect and a matrix implant.
Figure 2:
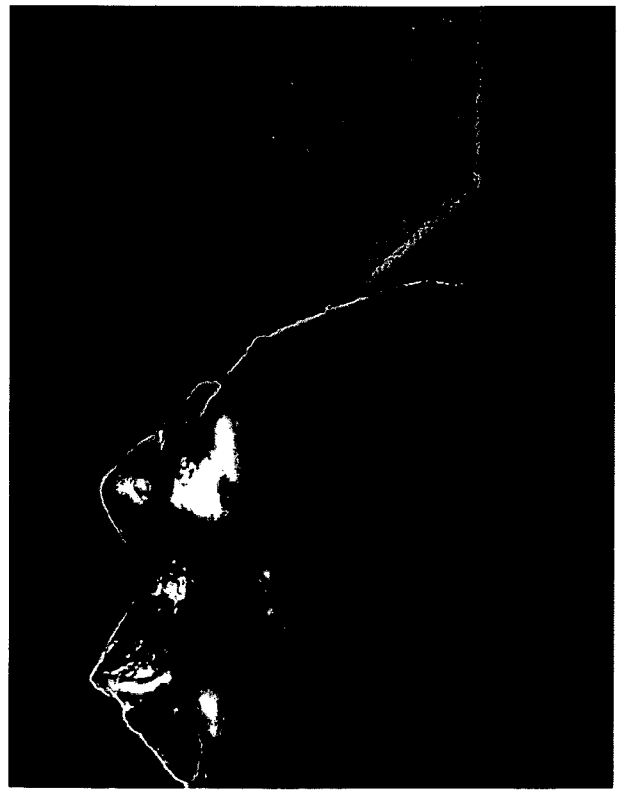

This example illustrates healing three months after the intervention illustrated in Example 2. FIG. 2 shows an example of gross outcome at 3 months. Gross image of the femoral condyle (FIG. 2a) and cross section of the tissue at the defect site (FIG. 2b) reveals new tissue formation fully integrated with the native cartilage and no evidence of inflammation at the site. FIG. 2b is a cross section of the implant site after decalcification showing extensive ingrowths and replacement of the implant with cartilage and bone. Animals having similar defects but not receiving an entangled polyester-polysaccharide matrix do not show the same extent of ingrowth of cartilage and bone.

Example 4

Figure 3:
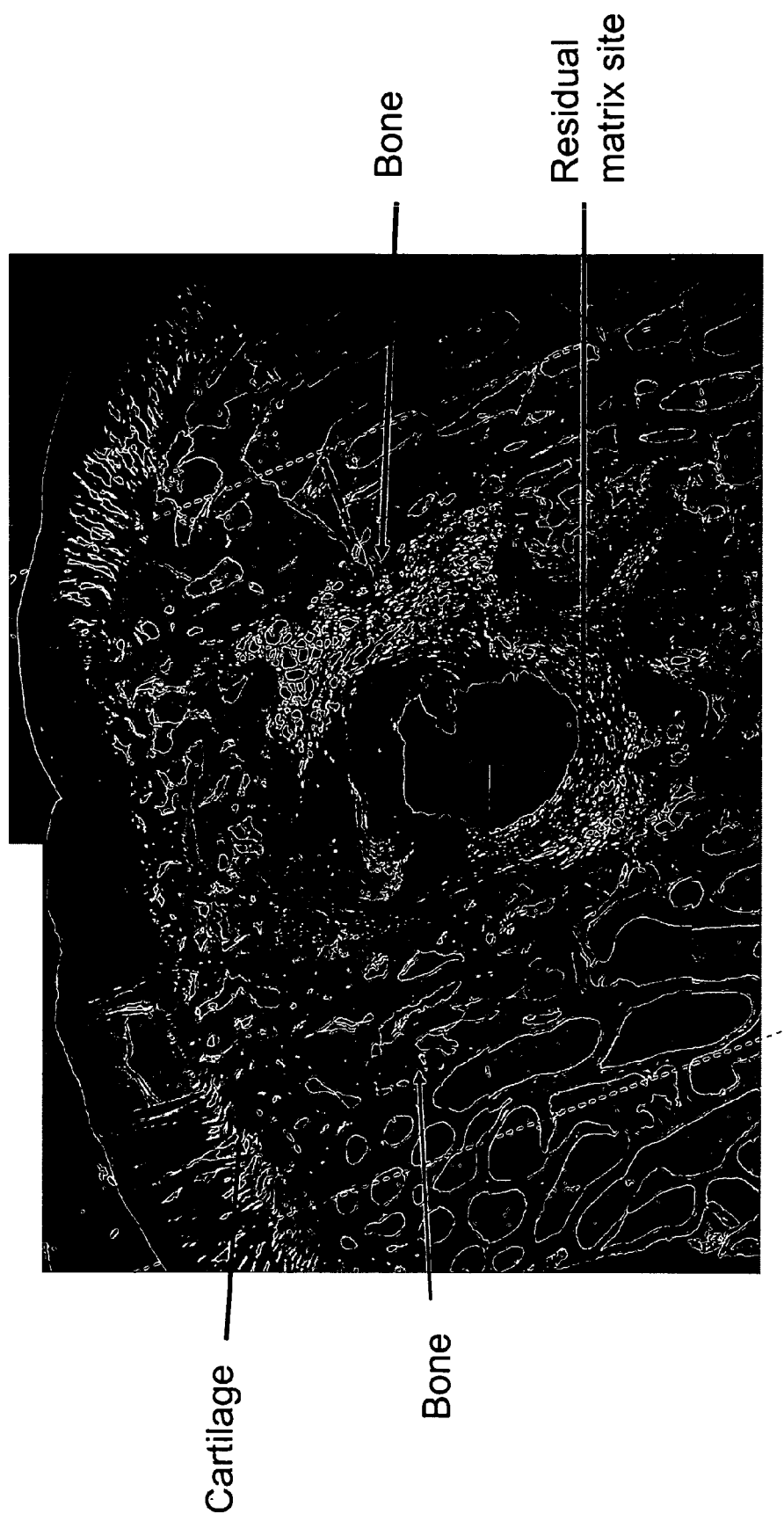
FIG. 3 illustrates histological analysis of osteochondral tissue in a sheep three months after introduction of a circular defect and a matrix implant, including demonstration of hyaline cartilage and bone repair.

This example illustrates histological analysis of the 3-month post-intervention tissue presented in Example 3, and demonstrates hyaline cartilage repair with active osteogenesis at the core of the implant. In this example, as shown in FIG. 3, the tissue was stained with Safranin-O to visualize the cartilage proteoglycans found in the native and newly formed cartilage. FIG. 3 indicates that new cartilage and bone at the site of intervention become recognizable histologically upon examination 3 months following the procedure. FIG. 3 further indicates that greater than 50% of the composite implant was degraded/resorbed by 3 months post-intervention and was replace by newly formed bone and cartilage. Dashed line shows the marking of the surgical defect.

Example 5

Figure 4:
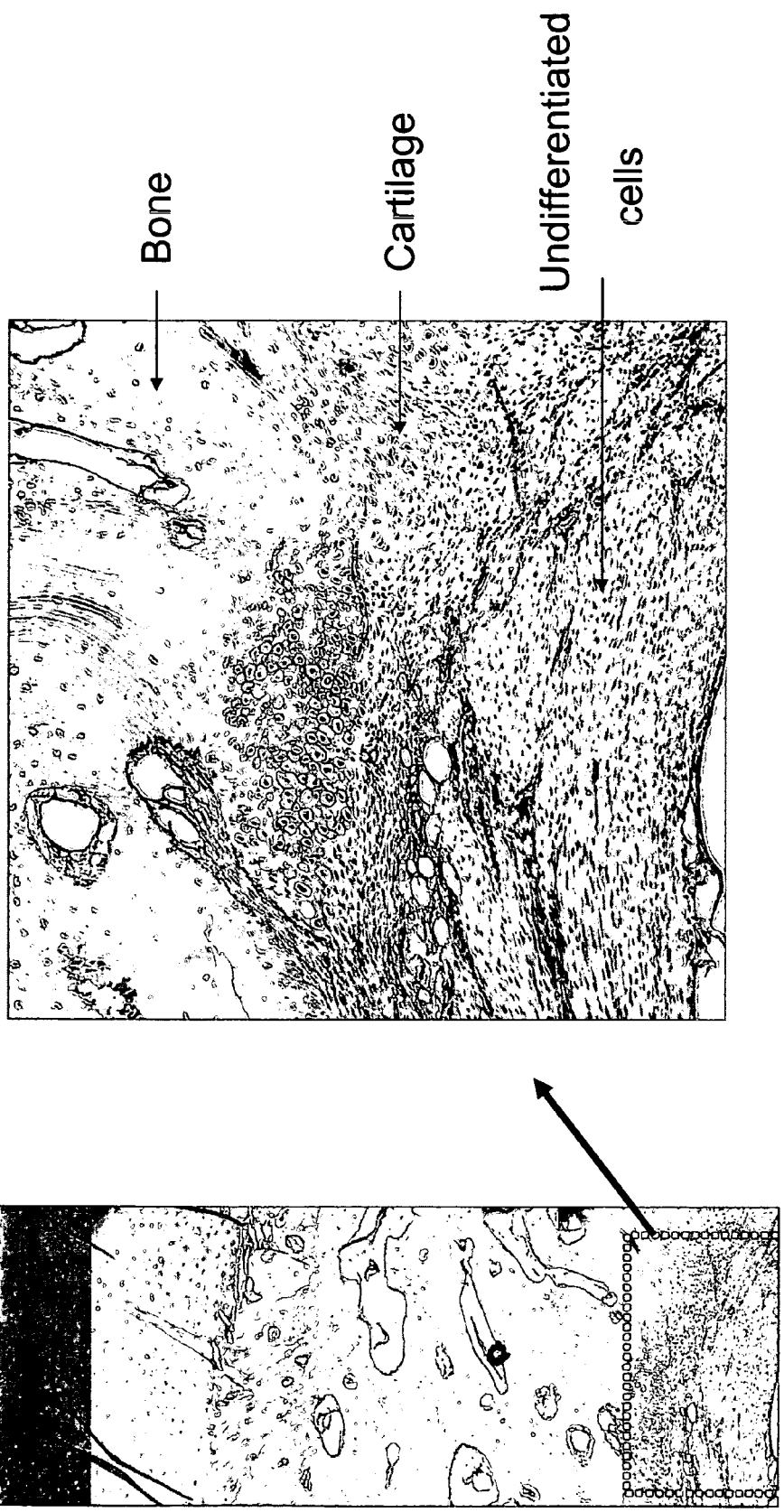
FIG. 4 illustrates endochondral bone formation at implant interface in a sheep three months after introduction of a circular defect and a matrix implant.

This example illustrates formation of cartilage and bone three months post-intervention. As shown in FIG. 4, light microscopy of an area close to the implant site reveals active formation of cartilage from undifferentiated stem cells derived from marrow cavity, and remodeling and formation of endochondral bone. Endochondral bone formation can be seen at implant interface.

Example 6

Figure 5:
FIG. 5 illustrates gross morphology in a medial femoral condyle of a sheep six months after introduction of a circular defect and a matrix implant.
Figure 5:
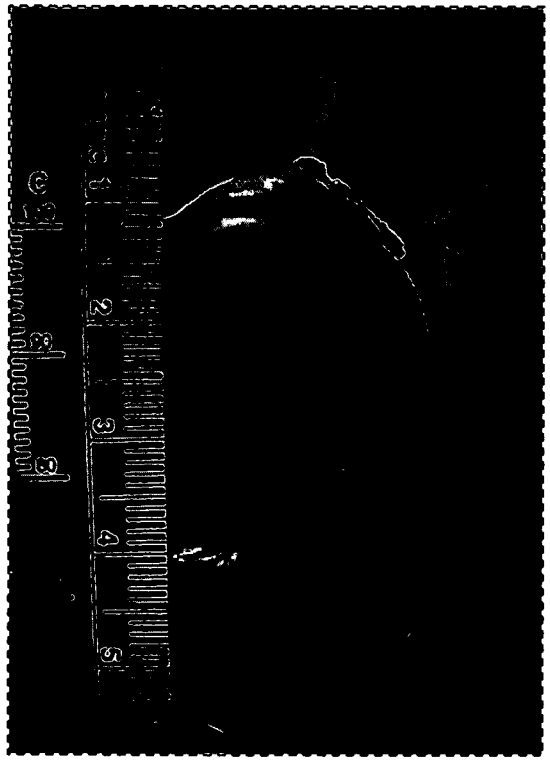

This example illustrates healing six months after the intervention illustrated in Example 2. FIG. 5 shows an example of gross outcome at 6 months post intervention. FIG. 5a shows gross images of the joint surface, while FIG. 5b shows a cross section of the tissue at the defect site. This figure demonstrates that healing of the osteochondral defect continued to improve from 3 to 6 months post-intervention. The healed tissue shows excellent integration and bonding with the native cartilage and bone, and over 90% of the implanted material is replaced with newly formed tissue.

Example 7

Figure 6:
FIG. 6 illustrates histological analysis of osteochondral tissue in a sheep six months after introduction of a circular defect and a matrix implant, including demonstration of more extensive hyaline cartilage and bone repair compared to a femoral condyle three months after receiving a circular defect and a matrix implant.

This example illustrates histological analysis of the 6-month post-intervention tissue presented in Example 6. As shown in FIG. 6, tissue was stained with Safranin-O to visualize staining of the cartilage proteoglycans found in the native and newly formed cartilage. FIG. 6 illustrates that greater than 90% of the implanted material was replaced with newly formed cartilage and bone.

Example 8

This example illustrates soft tissue contour augmentation.
In this example, a patient presents with extensive facial wrinkles. An injectable formulation comprising an entangled polyester-polysaccharide matrix comprising PLA-PGA copolymer and hyaluronic acid is injected by a dermatologist within the dermis at sites of facial wrinkles. Improvements in appearance, i.e., diminishment of wrinkling, is observable to a casual observer within three months after injection.

Example 9

This example illustrates an anterior lumbar interbody fusion or (ALIF) spinal fusion using an interbody cage and a paste of the present teachings.

In this example, a trained individual such as a surgeon, inserts an interbody cage into the anterior aspect of the spine. The cage, which is a cylinder made of porous titanium, is inserted through a small incision (minilaparotomy), although an endoscope can also be used that allows the surgery to be done using a series of small incisions. Following insertion, the cage is filled with a paste comprising a matrix comprised of polyester entangled with hyaluronic acid, and further comprising a bone morphogenetic protein, recombinant human bone morphogentic protein-2 (rhBMP-2). The cage permits growth of a bone graft from a vertebral body through the cage, into the adjacent vertebral body. Patient recovery is significantly more rapid using this technique compared to a similar procedure omitting the matrix.

Example 10

This example illustrates formation of a paste.
In this example, a mixture is formed, comprising 100 grams of granules of a matrix prepared as in Example 1 and an equal weight of an aqueous solution comprising hyaluronic acid (2% w/w). The components are blended in a microcutter for 10 minutes, yielding a viscous paste.

It is to be understood that while some of the examples and descriptions may include some conclusions about the way a matrix may function, the inventors do not intend to be bound by those conclusions and functions, but put them forth only as possible explanations.

It is to be further understood that specific embodiments of the present teachings as set forth herein are not intended as being exhaustive or limiting, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims. In addition, examples described above are illustrative only and are not intended to limit the scope of the claims.

All references cited in this specification are hereby incorporated by reference. Any discussion of references cited herein is intended merely to summarize the assertions made by their authors. No admission is made that any reference or portion thereof constitutes relevant prior art. Applicants reserve the right to challenge the accuracy and pertinence of the cited references.

What is claimed is:

1. A method of promoting tissue growth at a tissue site in need of tissue growth in a mammal in need thereof, the method comprising injecting an injectable tissue matrix composition at the site, wherein the injectable matrix composition comprises polyester polymers entangled with hyaluronic acid polymers by a process comprising the steps of: (i) dissolving the polyester polymers in an organic solvent; (ii) blending the polyester polymers with hyaluronic acid polymers contained in an aqueous medium to form an emulsified mixture; and (iii) pouring the emulsified mixture of the two polymers into a mold, (iv) successively removing the organic solvent and water from the mold to form a solid matrix comprising the polyester polymers entangled with the hyaluronic acid polymers; (v) granulating the solid matrix to form matrix granules; and (vi) combining the matrix granules with an aqueous liquid solution comprising hyaluronic acid to form a paste or a viscous liquid capable of injection at the tissue site.

2. The method of claim 1, wherein the matrix composition comprises a paste.

3. The method of claim 1, wherein the matrix composition comprises a viscous liquid.

4. The method of claim 1, wherein the mammal is a human in need of treatment.

5. The method of claim 1, wherein the site in need of tissue growth comprises bone and periosteal tissue.

6. The method of claim 1, wherein the tissue growth comprises facial contour augmentation.

7. The method of claim 1, wherein the matrix further comprises at least one therapeutic agent.

8. The method of claim 7, wherein the at least one therapeutic agent is selected from the group consisting of an anti-infective agent, a pain medication, an analgesic, an anti-inflammatory agent, and an immunosuppressive agent.

9. The method of claim 1, wherein the site in need of tissue growth comprises bone and a periodontal ligament.

10. The method of claim 1, wherein the site in need of tissue growth comprises bone and cartilage.

11. The method of claim 1, wherein the site in need of tissue growth comprises bone and hyaline cartilage.

12. The method of claim 11 wherein the hyaline cartilage is costal cartilage.

13. The method of claim 1, wherein the site in need of tissue growth comprises bone and fibrous cartilage.

14. The method of claim 13 wherein the fibrous cartilage is meniscus cartilage.

15. The method of claim 1, wherein the polyester polymers and hyaluronic acid polymers are combined at a weight ratio of polyester polymers to hyaluronic polymers of between 9:1 and 1:9.

16. The method of claim 1, wherein the matrix composition is characterized by (i) retention of pore structure and shape when hydrated, and (ii) the ability to support the growth of cells in vivo or ex vivo.

17. The method of claim 1, wherein the site in need of tissue growth is selected from the group consisting of bone tissue, cartilage tissue, tendon tissue, ligament tissue, vascular tissue, dermal tissue, periodontal tissue, intervertebral disc tissue, hyaline cartilage, fibrous cartilage, elastic cartilage, a nerve tunnel or a combination thereof.

* * * * *